United States Patent
Mechler et al.

(10) Patent No.: US 11,959,027 B2
(45) Date of Patent: *Apr. 16, 2024

(54) OILFIELD NATURAL GAS PROCESSING AND PRODUCT UTILIZATION

(71) Applicant: Chrisma Energy Solutions, LP, Amarillo, TX (US)

(72) Inventors: Thomas Richard Mechler, Amarillo, TX (US); Melea Rachel Bonasso, Florence, TX (US)

(73) Assignee: Chrisma Energy Solutions, LP, Amarillo, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/119,190

(22) Filed: Mar. 8, 2023

(65) Prior Publication Data
US 2023/0242823 A1 Aug. 3, 2023

Related U.S. Application Data

(62) Division of application No. 16/862,402, filed on Apr. 29, 2020, now Pat. No. 11,634,646.

(60) Provisional application No. 62/840,245, filed on Apr. 29, 2019.

(51) Int. Cl.
| | |
|---|---|
| *C10G 5/06* | (2006.01) |
| *C07C 7/14* | (2006.01) |
| *C10L 3/10* | (2006.01) |
| *C10L 3/12* | (2006.01) |
| *F25J 3/02* | (2006.01) |

(52) U.S. Cl.
CPC .......... *C10G 5/06* (2013.01); *C07C 7/14* (2013.01); *C10L 3/10* (2013.01); *C10L 3/12* (2013.01); *F25J 3/0209* (2013.01); *C10G 2300/1025* (2013.01); *C10G 2300/308* (2013.01); *F25J 2220/64* (2013.01); *F25J 2230/30* (2013.01); *F25J 2290/62* (2013.01); *F25J 2290/70* (2013.01)

(58) Field of Classification Search
CPC ... C10G 5/06; C10G 5/00; C10G 5/04; C10G 5/02; C07C 7/14
See application file for complete search history.

(56) References Cited

U.S. PATENT DOCUMENTS

| | | | |
|---|---|---|---|
| 10,018,027 B2 * | 7/2018 | Graney, IV | C10L 3/101 |
| 2021/0246387 A1 * | 8/2021 | Koseoglu | C10G 45/44 |

* cited by examiner

*Primary Examiner* — Sharon Pregler
(74) *Attorney, Agent, or Firm* — John G. Fischer, Esq.; Scheef & Stone, L.L.P.

(57) ABSTRACT

A remote hydrocarbon processing system comprising a gas compressor skid, gas processing skid, electric power generation skid, liquid storage tank, blending skid, and crude oil source, are fluid flow interconnected and located proximate to a producing well. Produced gases are delivered from the well to the gas compressor skid. Compressed natural gas is delivered to the gas processing skid where it is thermally separated to generate a processed gas stream and a processed liquid stream. The processed gas stream is delivered to the electric power generation skid and burned to generate electricity that may be delivered to an electric power transmission line. The processed liquid stream is delivered to the liquid storage tank. Crude oil from the crude oil source and processed liquid stream from the liquid storage tank are delivered to the blending skid and blended into a lower viscosity, higher API gravity transportable crude oil.

5 Claims, 5 Drawing Sheets

OILFIELD NATURAL GAS PROCESSING AND PRODUCT UTILIZATION

RELATED U.S. APPLICATION DATA

This application is a divisional of U.S. application Ser. No. 16/862,402, filed Apr. 29, 2020, and which claimed the benefit of priority to Provisional Application No. 62/840,245, filed Apr. 29, 2019.

TECHNICAL FIELD OF THE INVENTION

The embodiments of the present disclosure relate to either onshore or offshore recovery of hydrocarbon liquids (also known as natural gas liquids or NGLs) by way of portable gas processing skids and involve the selective separation of the NGLs in the oilfield (or offshore) for disposition of the composite streams and the utilization of the remaining hydrocarbon gas as fuel gas for electric power generation.

BACKGROUND OF THE INVENTION

In the exploration of oil, gas and geothermal energy, drilling operations are used to create boreholes, or wells, in the earth. Wells drilled in subterranean exploration are often remotely located in rough terrain. Historically, hydrocarbons are most valuable in their liquid state.

Natural gas is produced either directly from gas wells (non-associated produced gas) or from oil well associated produced gas (natural hydrocarbon gas produced in conjunction with crude oil producing wells). For the last several decades, natural gas has been gathered through pipelines either from a conventional tank battery for oil producing wells, or from natural gas wells, and transported to centralized gas processing plants. As used in this description and conventional to the industry, a tank battery is a field production facility located near subterranean hydrocarbon wells whose purpose is to separate produced fluids into three naturally occurring components: crude oil, natural gas, and produced water.

These plants first remove water vapor and other impurities. The water vapor may be removed with a dehydration unit or by other means conventionally known and also may be treated chemically. As used in this description and conventional to the industry, water vapor describes naturally occurring water molecules entrapped in the produced natural gas. The dehydrated stream is then processed to separate the hydrocarbon liquids. As used in this description and conventional to the industry, a dehydrated stream is produced natural gas with water vapor removed. Hydrocarbon liquids (also known as natural gas liquids (NGLs), Y-grade or condensate) frequently consist of ethane, propane, iso-butane, normal-butane, and pentanes and heavier hydrocarbon liquids (pentane+) separated from methane (often called residue gas) present in the produced natural gas. This is accomplished by way of gas processing units known as demethanizers.

The NGLs are then transported in a transmission pipeline, frequently over great distances, to a fractionation plant. At the fractionation plant, the NGLs are separated (such as by cryogenic process) into pure products for their ultimate sale and distribution.

The remaining residue gas (methane) is sold and transported from the plant into gas transmission pipelines for use commercially such as for residential heating or electric power plant fuel (see FIG. 1). The pentanes and heavier hydrocarbon liquids are also called natural gasoline within the industry and are most often sold to refineries. As used in this description and conventional to the industry, pentane and heavier hydrocarbon liquids are designated as pentane+. The entire process is expensive, requiring significant capital and high operating expenses, and incorporates safety and environmental risks as wells as inefficiencies associated with the transportation, distribution, and secondary transportation of fuels.

Rapidly declining oil wells are frequently found in oil shale production areas, where production decline rates can be as much as 75% or more over eighteen months. One of the challenges for companies owning and operating centralized gas processing plants (which process the produced gas from the oil wells) is that plant and gathering line capacities have to be constructed to accommodate high volumes of natural gas initially produced. High-capacity construction becomes underutilized as production rates decline. Additionally, there is often a lack of pipeline capacity in remote locations where many wells are drilled. More recently, fractionation plants are at full capacity, limiting a gas purchaser's opportunity to remove and utilize associated produced gas economically. As a result, some onshore and offshore producers of associated natural gas have had few alternatives for the disposition of the produced gas other than flaring.

In other cases, high concentrations of localized oil well development exceeds gas processing and/or pipeline capacity which has resulted in operators of many new wells being required to flare associated produced gas (see FIG. 2). As used in this description and conventional to the industry, gas processing is the utilization of equipment to separate various hydrocarbon components from natural gas. Not only is natural gas flaring a significant waste of valuable natural resources, it may also present significant environmental consequences. One such consequence is that when a relatively clean burning energy resource is wasted, the negative environmental impact is fully realized without any offsetting benefit. Another consequence is that an equivalent amount of the wasted energy must be produced by another energy source, such as burning coal, which may be far more detrimental to the environment.

There remains a need for an improved approach to the collection and processing of associated produced gas from the point of extraction to final disposition that improves efficiency, reduces waste and transportation risks, and minimizes environmental impact.

The several embodiments of the present disclosure provide unique solutions to the engineering constraints and challenges of treatment, separation, and utilization of associated produced gas in a manner that reduces the risk and cost of transportation, improves economic value of recovered liquid and gaseous hydrocarbons, and significantly reduces waste and minimizes environmental damage.

SUMMARY OF THE INVENTION

The present disclosure provides a new system for remote treatment, separation, and utilization of wellsite produced hydrocarbons. Conventional practice involves commingling produced natural gas from gas gathering lines from multiple wells in a natural gas producing field and transporting the commingled product to centralized gas processing plants for processing. As used in this description and conventional to the industry, produced natural gas may include non-associated produced gas and/or associated produced gas. In the novel processes disclosed, modularized processing skid-based facilities, process sized to accommodate the well's declining production rates, are utilized. The NGLs recovered from such skids are separated into specific streams of segregated liquid hydrocarbons and gaseous hydrocarbons in the field or offshore.

In a first embodiment of the invention, a remote hydrocarbon processing system for use on remotely located gas producing wells to reduce resource waste and adverse environmental impact is disclosed. The system comprises a gas compressor skid positioned proximate to a natural gas or associated gas producing well and configured to receive, dehydrate, and compress produced natural gas from the well. A gas processing skid is gas flow connected to the gas compressor skid and configured for thermal separation of compressed natural gas received from the gas compress or skid into a first processed gas stream and a first processed liquid stream.

A power generation skid is gas flow connected to the gas processing skid and configured to generate electricity from the first processed gas stream received from the gas processing skid. A liquid storage tank is liquid flow connected to the gas processing skid and configured for pressurized storage of the first liquid stream. A blending skid is liquid flow connected to the liquid storage tank and liquid flow connected to a crude oil supply source. The blending skid is configured for controlled blending of the first processed liquid stream received from the liquid storage tank with crude oil received from the crude oil supply source to form a modified crude oil product having a higher API gravity and a lower viscosity than the supplied crude oil.

In another embodiment, the processing gas skid is configured for thermal separation of the compressed natural gas into a first processed gas stream having four carbon chain molecules or less, and a first processed liquid stream having five carbon chain molecules or more.

In another embodiment, the gas processing skid is configured for thermal separation of the compressed natural gas into a first processed gas stream having three carbon chain molecules or less, and a first processed liquid stream having four carbon chain molecules or more.

In another embodiment, the gas processing skid is configured for thermal separation of the compressed natural gas into a first processed gas stream having two carbon chain molecules or less, and a first processed liquid stream having three carbon chain molecules or more.

In another embodiment, the modified crude oil product is blended to be within allowable crude oil transportation specifications.

In another embodiment, the gas compressor skid further comprises a liquid removal unit and an electric motor driven compressor. In another embodiment, the gas processing skid further comprises a heat exchanger, a chiller, and a cold separator. In another embodiment, the power generation skid is a gas driven electrical power generation skid having a gas turbine and an electric generator.

In another embodiment, the power generation skid is electricity connected to an electric power transmission line that is electrically connected to an electrical substation located within a Competitive Renewable Energy Zones (CREZ) line zone.

In another embodiment, the blending skid further comprises a first metering valve for metering the amount of the first processed liquid stream blended with the supplied crude oil, and a second metering valve for metering the amount of supplied crude oil blended with the first processed liquid stream.

In another embodiment, a remote hydrocarbon processing system for use on remotely located gas producing wells is disclosed, comprising a gas compressor skid positioned proximate to a natural gas or associated gas producing well and configured to receive, dehydrate, and compress natural gas from the well.

A gas processing skid is gas flow connected to the gas compressor skid and configured for thermal separation of compressed natural gas received from the gas compressor skid into a first processed gas stream, a first processed liquid stream, and a second processed liquid stream. A power generation skid is gas flow connected to the gas processing skid and configured to generate electricity from the first processed gas stream received from the gas processing skid.

A first liquid storage tank is liquid flow connected to the gas processing skid and configured for pressurized storage of the first liquid stream. A second liquid storage tank is liquid flow connected to the gas processing skid and configured for pressurized storage of the second liquid stream. A blending skid is liquid flow connected to the first liquid storage tank and to a crude oil supply source.

The blending skid is configured for controlled blending of the first processed liquid stream received from the first liquid storage tank with crude oil received from the crude oil supply source to form a modified crude oil product having a higher API gravity and lower viscosity than the supplied crude oil. The second liquid storage tank is configured for pressurized storage of Liquified Petroleum Gas (LPG).

In another embodiment, a method of processing hydrocarbon products on remote wells is disclosed, comprising the steps of:

Providing a gas compressor skid proximate to a natural gas or associated gas producing well. Providing a gas processing skid proximate to the gas compressor skid. Providing a power generation skid proximate to the gas processing skid. Providing a liquid storage tank proximate to the gas processing skid.

Providing a blending skid proximate to the liquid storage tank. Providing a crude oil source proximate to the blending skid. Delivering natural gas from the producing well to the gas compressor skid. Delivering compressed natural gas from the gas compressor skid to the gas processing skid. Thermally separating the compressed natural gas into two hydrocarbon streams being a first processed gas stream and a first processed liquid stream.

Delivering the first processed gas stream to the power generation skid. Burning the first processed gas stream in a turbine on the power generation skid to drive an electrical generator to generate electricity.

Delivering the first liquid stream from the gas processing skid to the liquid storage tank. Delivering the first processed liquid stream from the liquid storage tank to the blending skid. Delivering crude oil from the crude oil source to the blending skid.

Blending the first processed liquid stream with the crude oil from the crude oil supply source to form a modified crude oil product having a higher API gravity and lower viscosity than the supplied crude oil.

In another embodiment, the step of thermally separating the compressed natural gas further comprises separating the natural gas into a first processed gas stream having four carbon chain molecules or less, and a first processed liquid stream having five carbon chain molecules or more.

In another embodiment, the step of thermally separating the compressed natural gas further comprises separating the natural gas into a first processed gas stream having three carbon chain molecules or less, and a first processed liquid stream having four carbon chain molecules or more.

In another embodiment the step of thermally separating the compressed natural gas further comprises, separating the natural gas into a first processed gas stream having two carbon chain molecules or less, and a first processed liquid stream having three carbon chain molecules or more.

In another embodiment, the modified crude oil product is blended to be within allowable crude oil transportation specifications.

In another embodiment, a method of processing hydrocarbon products on remote wells is disclosed, comprising the steps of:

Providing a gas compressor skid proximate to a natural gas or associated gas producing well. Providing a gas processing skid proximate to the gas compressor skid. Providing a power generation skid proximate to the gas processing skid. Providing a first liquid storage tank proximate to the gas processing skid.

Providing a second liquid storage tank proximate to the gas processing skid. Providing a blending skid proximate to the liquid storage tank. Providing a crude oil source proximate to the blending skid.

Delivering natural gas from the producing well to the gas compressor skid. Delivering compressed natural gas from the gas compressor skid to the gas processing skid. Thermally separating the compressed natural gas into three hydrocarbon streams being a first processed gas stream, a first processed liquid stream, and a second processed liquid stream.

Delivering the first processed gas stream to the power generation skid. Burning the first processed gas stream in a turbine on the power generation skid to drive an electrical generator to generate electricity.

Delivering the first processed liquid stream from the gas processing skid to the first liquid storage tank. Delivering the first processed liquid stream from the first liquid storage tank to the blending skid. Delivering crude oil from the crude oil source to the blending skid. Blending the first processed liquid stream with the crude oil from the crude oil supply source to form a modified crude oil product having a higher API gravity and lower viscosity than the supplied crude oil. Delivering the second processed liquid stream from the gas processing skid to the second liquid storage tank.

In another embodiment, the step of thermally separating the compressed natural gas further comprises separating the natural gas into a first processed gas stream having two carbon chain molecules or less, a first processed liquid stream having five of more carbon chain molecules, and a second processed liquid stream having between three and four carbon chain molecules.

In another embodiment, the second processed liquid stream comprises liquified petroleum gas (LPG).

As used in this description and conventional to the industry, the combination of propane, butanes and natural gasoline are designated as propane+.

All composite liquid streams may include various other hydrocarbon liquid components in minor amounts.

As used herein, "proximate" is intended to mean "near to the well(s)", "in the vicinity", and "not remote". As used herein, a "fluid connection" means a liquid or gas connection, as may be required.

A primary advantage of the invention is that it eliminates the need to transport NGLs to a fractionation or cryogenic plant and the requirement to transport the residue gas to other end users. Another advantage of the invention is that these conventional options remain available should there be an economic benefit to utilize this approach for the remaining hydrocarbon liquids after the natural gasoline has been extracted and blended into crude oil.

Another advantage the invention provides is processing flexibility by enabling utilization of hydrocarbon components that are lighter than pentanes in the most economically feasible manner based on their value either as a gas for use as electric power generation fuel, or as a liquid in the case of propane and butanes to be sold as LPG (See FIG. 4). Another advantage of the invention is it provides highly valued utilization of the butanes when included with the pentane+ and blended into the crude oil and ultimately transported to a refinery when pipeline specifications allow (see FIGS. 3 and 5).

Another advantage of the invention is should the local crude oil transmission pipeline specifications prohibit the utilization of the propane and/or butanes as a blending component, the product may be sold as LPG. Another advantage of the invention is that should a profitable LPG market not be available, the composite stream of butanes and lighter hydrocarbon gas may be utilized as gas engine (or gas turbine) fuel for the generation of and ultimate sale of electricity.

Another advantage of the invention is that it provides the above listed advantages while eliminating the wasteful and environmentally harmful practice of flaring natural gas from wells producing oil (or condensate). The invention utilizes the previously wasted natural gas as fuel gas for electric power generation. The generated electricity is then used locally or introduced into the power transmission grid.

BRIEF DESCRIPTION OF THE DRAWINGS

The objects and features of the invention will become more readily understood from the following detailed description and appended claims when read in conjunction with the accompanying drawings in which like numerals represent like elements.

The drawings constitute a part of this specification and include exemplary embodiments to the invention, which may be embodied in various forms. It is to be understood that in some instances various aspects of the invention may be shown exaggerated or enlarged to facilitate an understanding of the invention.

DETAILED DESCRIPTION OF THE PREFERRED EMBODIMENTS

The following description is presented to enable any person skilled in the art to make and use the invention and is provided in the context of a particular application and its requirements. Various modifications to the disclosed embodiments will be readily apparent to those skilled in the art, and the general principles defined herein may be applied to other embodiments and applications without departing from the spirit and scope of the present invention. Thus, the present invention is not intended to be limited to the embodiments shown but is to be accorded the widest scope consistent with the principles and features disclosed herein.

To the extent the following description of an embodiment suggests equipment certain details or options, it is to be understood that those details and options are disclosed for all embodiments.

Figure 1:
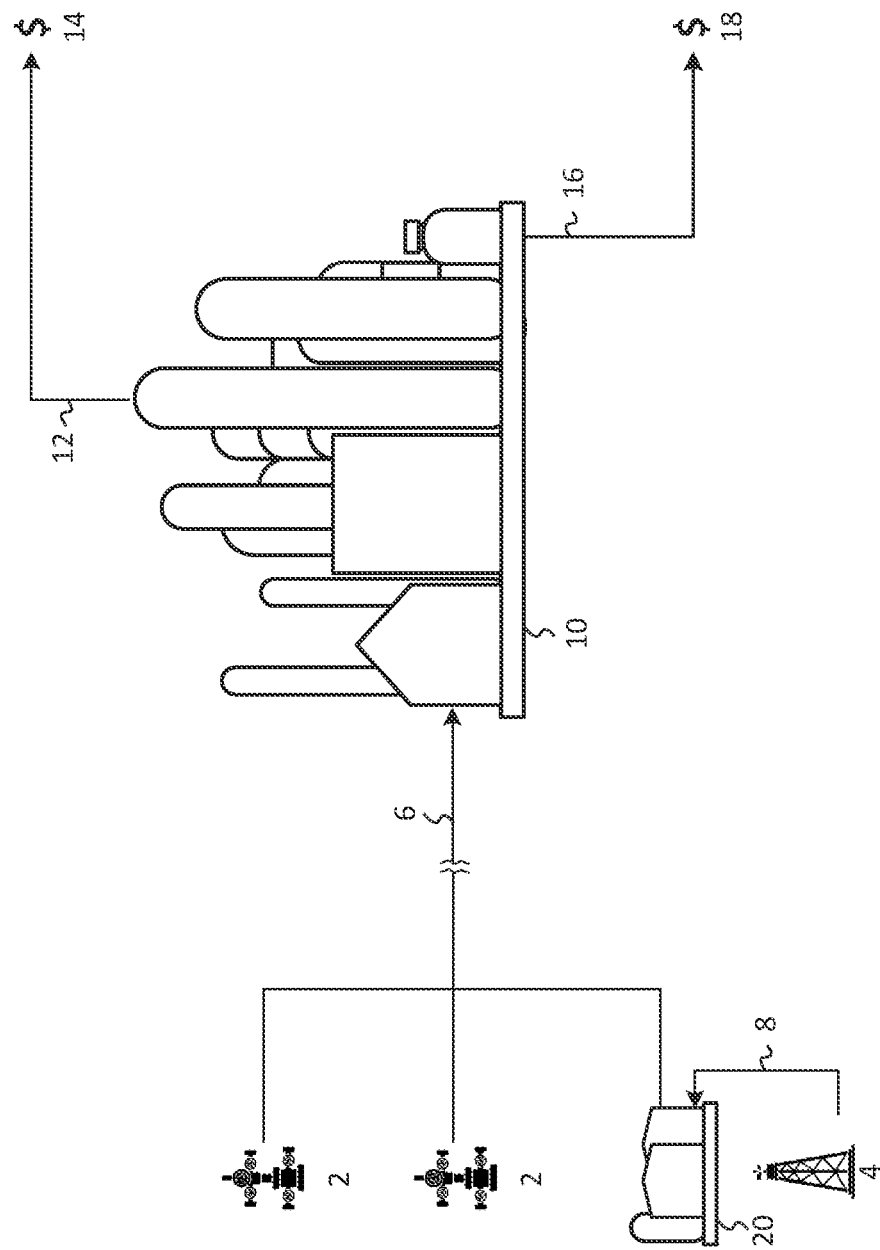
FIG. 1 is a schematic flow diagram of conventional disposition of natural gas produced from a wellhead and/or a tank battery and delivered to a conventional centralized gas processing plant.

FIG. 1 is a schematic flow diagram for the disposition of natural gas 6 produced from wellhead 2 and/or tank battery 20 and delivered to a conventional centralized gas processing plant 10.

As shown in FIG. 1, produced natural gas from a wellhead 2 and/or tank battery 20 is piped into gas gathering lines 6 and brought across many miles to a centralized gas processing plant 10. After gas processing is completed, methane and incidental ethane (residue gas) 12 is transferred to methane and incidental ethane (residue gas) sales 14. Remaining ethane and heavier natural gas liquids (NGL) 16 are transferred to ethane and heavier natural gas liquids (NGL) sales 18.

Figure 2:
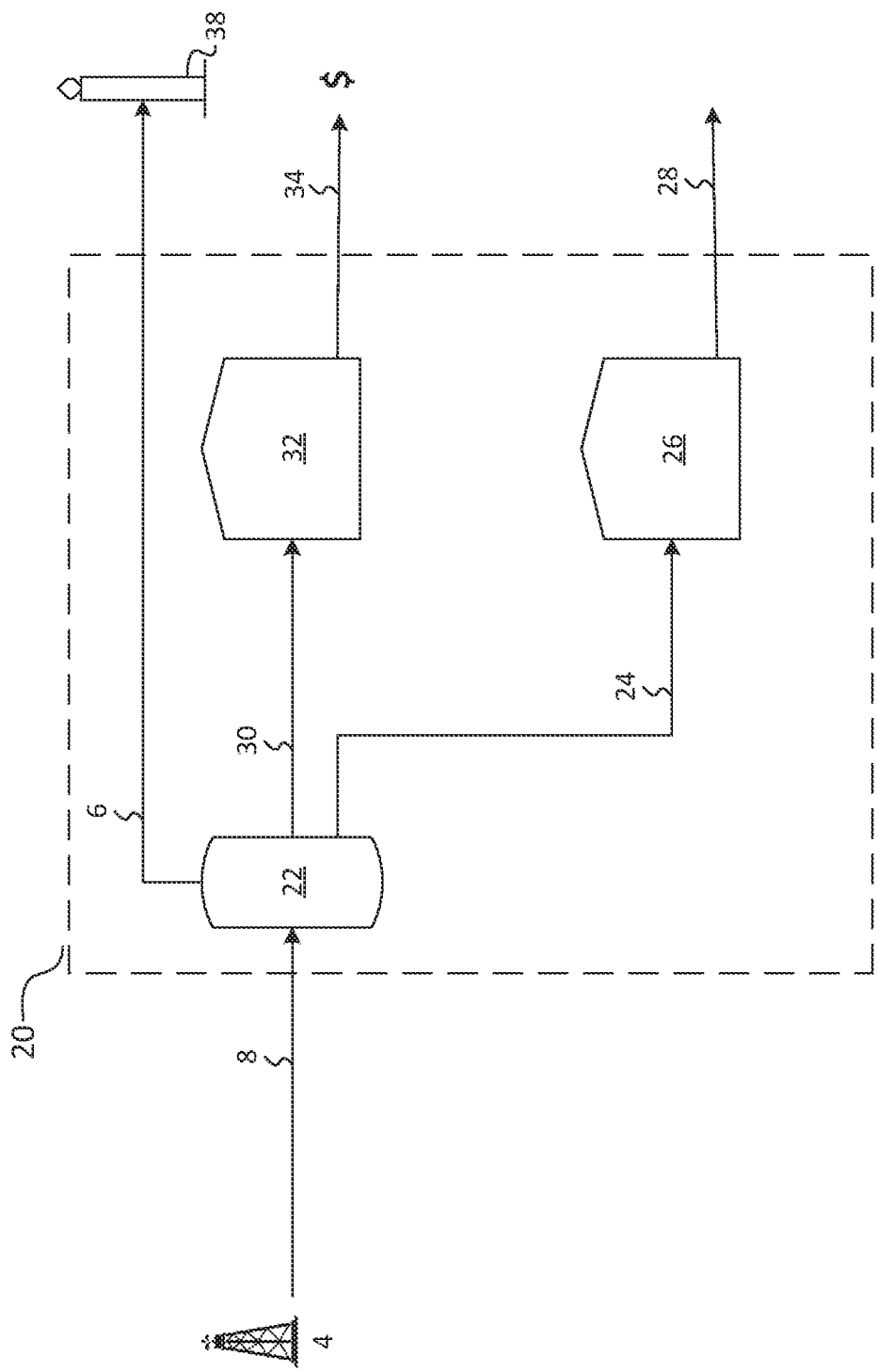
FIG. 2 is a schematic flow diagram of conventional disposition of crude oil and associated gas produced from an oil producing wellhead.

FIG. 2 is a schematic flow diagram of the disposition of associated gas produced from a crude oil producing wellhead 4 for the elimination of associated natural gas 6 via flaring 38 when the associated natural gas 6 cannot be transferred to centralized gas processing plant 10 as shown in FIG. 1.

As shown in FIG. 2, produced oil/gas/water composite fluid stream 8 from one or more oil wells enters a tank battery 20 having a 3-phase separator or treater 22 which separates the composite stream into individual fluids. As used in this description and conventional to the industry, fluids can either exist in a liquid phase or a gas phase. 3-phase separator 22 segregates each of produced water 24, crude oil 30, and associated natural gas 6.

Produced water 24 is transferred to produced water storage tank 26 for collection prior to transporting to water disposal 28 via truck or pipeline. Crude oil 30 is transferred to crude oil storage tank 32 for sale of crude oil 34. Associated produced gas 6 is transported to gas flare 38 to be burned, which results in no useful economic benefit and the byproducts of which are released into the atmosphere.

The disclosed invention provides a system and method for processing hydrocarbon products on remote wells to enhance the crude oil product, and to reduce resource waste and adverse environmental impact.

Figure 3:
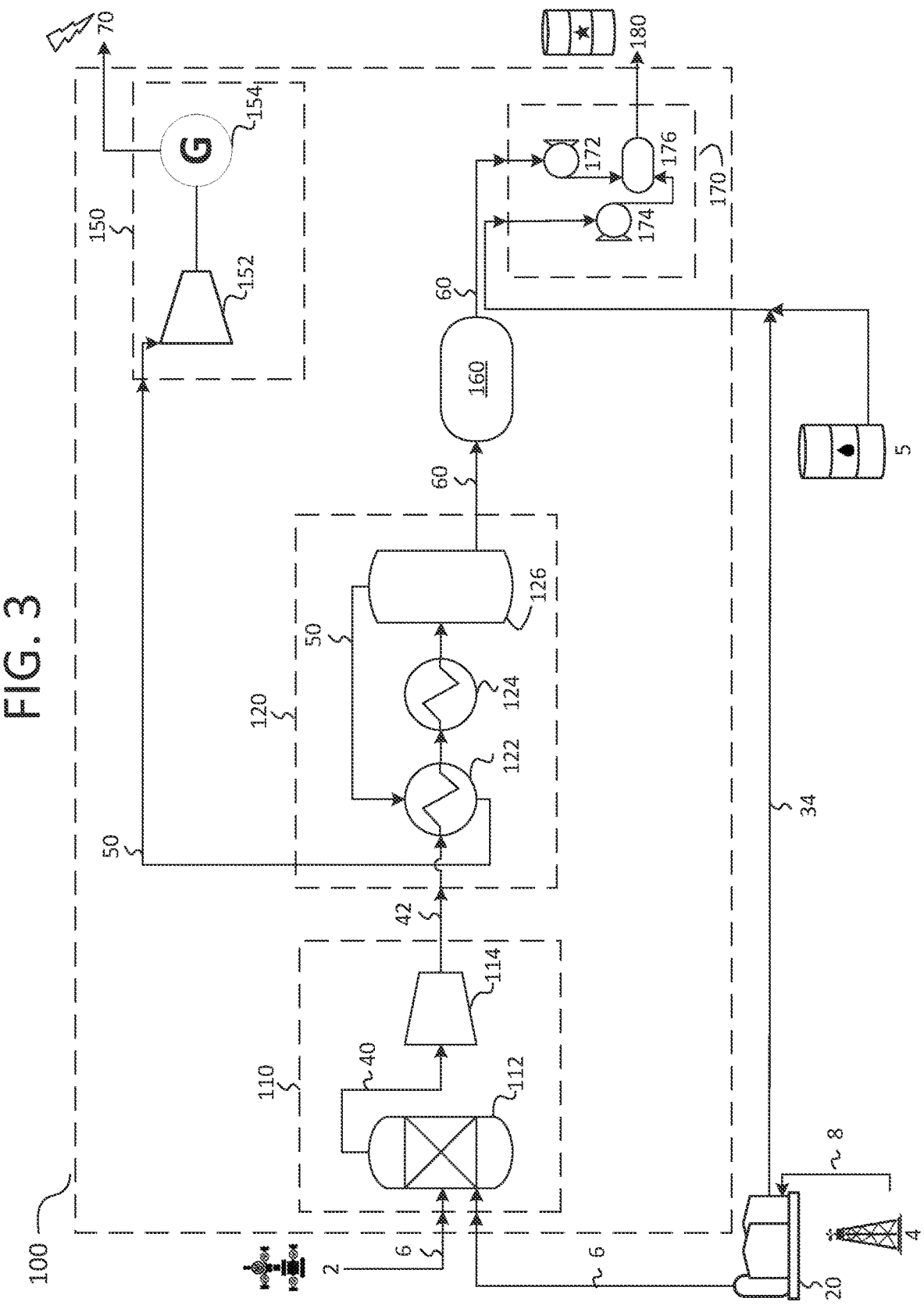
FIG. 3 is a schematic flow diagram of a first embodiment of the present invention in which a first processed gas stream and a first processed liquid stream are produced from the produced natural gas for remote utilization.

FIG. 3 illustrates a diagram of a first embodiment 100 of the invention. A remote hydrocarbon processing system 100 for use on remotely located gas producing wells 2 or oil producing wells 4 is provided to reduce resource waste and adverse environmental impact. Remote processing system 100 comprises a gas compressor skid 110 configured to receive, dehydrate, and compress natural gas 6 from well 2 or associated natural gas 6 from tank battery 20.

Produced natural gas 6 first passes through liquid removal unit 112 to minimize the possibility of liquid slugs damaging the gas compressor. The dry gas 40 exiting liquid removal unit 112 is compressed by compressor 114. Gas compressor skid 110 may comprise steel frames having piping, an inlet tank liquid scrubber, and an electric motor or gas engine driven prime mover (an initial electrical or mechanical source of motive power) connected to compressor 114.

A gas processing skid 120 is gas flow connected to gas compressor skid 110 and configured for thermal separation of compressed natural gas 42 received from gas compressor skid 110 into a first processed gas stream 50 and a first processed liquid stream 60. Gas processing skid 120 may comprise steel frames having dehydration equipment, liquid scrubbers, heat exchangers, refrigeration compressors, towers, piping, and other equipment. Gas processing skid 120 typically utilizes a mechanical separation—refrigeration design. Ancillary equipment may be utilized as necessary to purify and dehydrate compressed natural gas 42. Gas processing skid 120 is configured to separate the compressed natural gas 116 into two specific hydrocarbon streams A power generation skid 150, such as a gas driven electric power generation skid, is gas flow connected to gas processing skid 120 and configured to generate electricity from first processed gas stream 50 received from gas processing skid 120 or if additional secondary crude oil supply source 5 is needed to optimize blending.

A first liquid storage tank 160 is liquid flow connected to gas processing skid 120 and configured for pressurized storage of first processed liquid stream 60. A blending skid 170 is liquid flow connected to first liquid storage tank 160, and liquid flow connected to a crude oil supply 34 from the tank battery 20 of an oil producing well 4, to a secondary crude oil supply source 5 if remote processing system 100 is connected to a natural gas well 2.

Blending skid 170 is configured for controlled blending of the first processed liquid stream 60 received from first liquid storage tank 160 with crude oil 34 to form a modified crude oil product 180 having a higher API gravity and lower viscosity than crude oil 34. Blending skid 170 comprises one or more steel frames, and equipment including pumps and instruments for measuring hydrocarbon liquids and crude oil and for sampling and blending the liquids into a relatively homogeneous liquid.

In one embodiment, gas processing skid 120 is configured for thermal separation of the compressed natural gas 42 into a first processed gas stream 50 having four carbon chain molecules or less, and a first processed liquid stream 60 having five carbon chain molecules or more.

In another embodiment, gas processing skid 120 is configured for thermal separation of the compressed natural gas 42 into a first processed gas stream 50 having three carbon chain molecules or less, and a first processed liquid stream 60 having four carbon chain molecules or more.

In another embodiment, gas processing skid 120 is configured for thermal separation of the compressed natural gas 42 into a first processed gas stream 50 having two carbon chain molecules or less, and a first processed liquid stream 60 having three carbon chain molecules or more.

In another embodiment, the modified crude oil product 180 is blended to be within allowable crude oil transportation specifications.

In another embodiment, gas compressor skid 110 further comprises a liquid removal unit 112 and an electric motor driven compressor 114.

In another embodiment, gas processing skid 120 further comprises a gas-gas heat exchanger 122, a chiller 124, and a cold separator 126, and wherein cold separator 126 is gas flow connected to gas-gas heat exchanger 122 to provide cooling gas and to precool compressed natural gas 42 before delivery to chiller 124.

In another embodiment, blending skid 170 further comprises a first metering valve 172 configured to precisely control the flow of first processed liquid stream 60 to a blender 176 on blending skid 170, and a second metering valve 174 configured to precisely control the flow of crude oil 34 from tank battery 20 or secondary crude oil supply source 5 to blender 176.

In another embodiment, power generation skid 150 comprises a gas driven electrical power generation skid having a gas turbine 152 and an electrical generator 154. In another embodiment, power generation skid 150 is electrically connected to an electric power transmission line 70 that is electrically connected to an electrical substation located within a Competitive Renewable Energy Zones (CREZ) line zone, to permit sale of the generated electricity.

Figure 4:
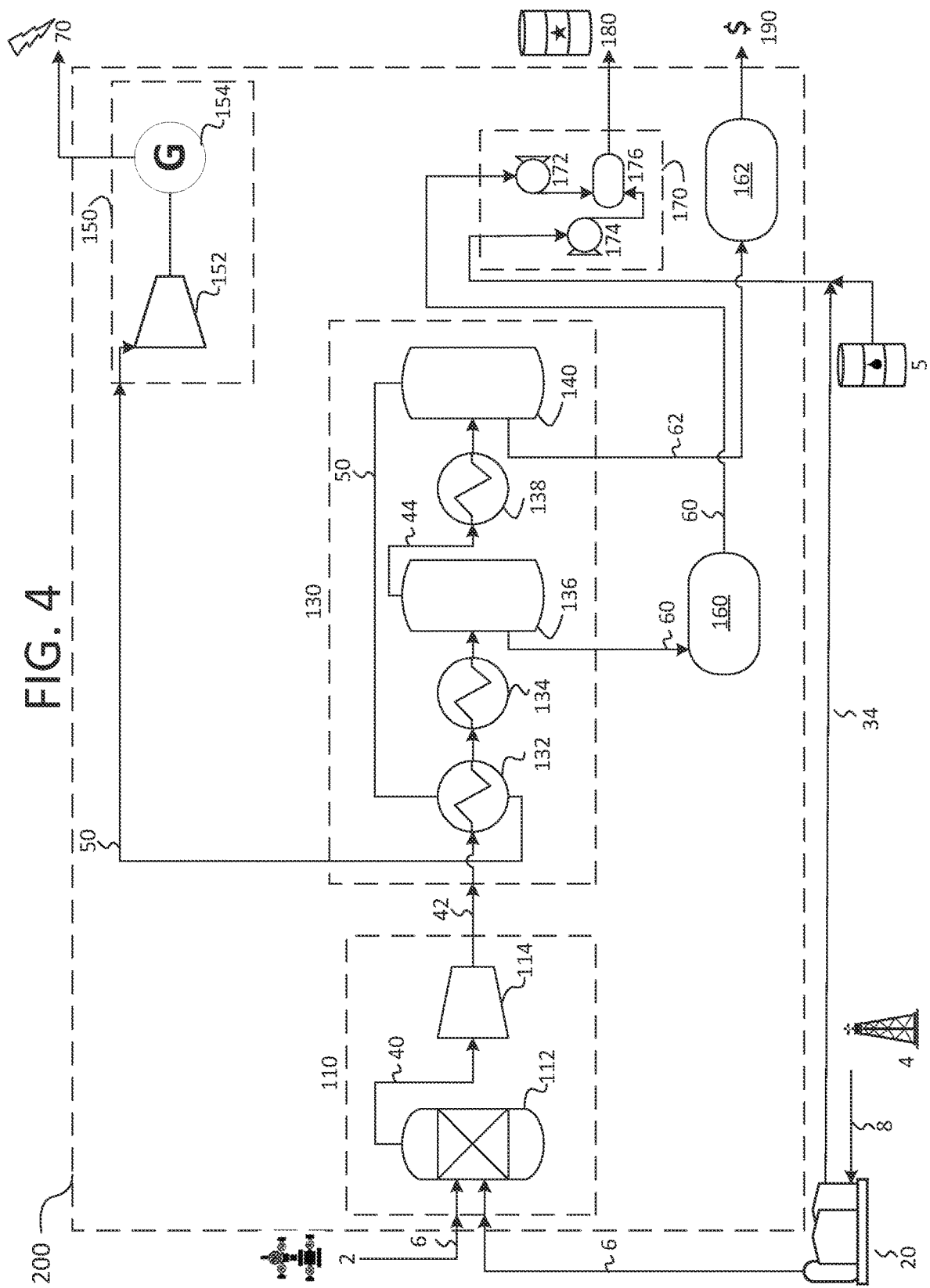
FIG. 4 is a schematic flow diagram of a second embodiment of the present invention in which a first processed gas stream, a first processed liquid stream, and a second processed liquid stream are produced from the produced natural gas for remote utilization.

FIG. 4 illustrates a diagram of a second embodiment 200 of the invention. A remote hydrocarbon processing system 200 for use on remotely located gas producing wells 2 or oil producing wells 4 is provided to reduce resource waste and adverse environmental impact. Remote processing system 200 comprises gas compressor skid 110 configured to receive, dehydrate, and compress natural gas 6 from well 2 or associate natural gas 6 from tank battery 20.

A gas processing skid 130 is gas flow connected to gas compressor skid 110 and configured for thermal separation of compressed natural gas 42 received from gas compressor skid 110 into a first processed gas stream 50, a first processed liquid stream 60, and a second processed liquid stream 62.

Power generation skid 150, such as a gas driven electric power generation skid, is gas flow connected 50 to gas processing skid 130 and configured to generate electricity from the first processed gas stream received from gas processing skid 130.

A first liquid storage tank 160 is liquid flow connected 60 to gas processing skid 130 and configured for pressurized storage of first processed liquid stream 60. A second processed liquid storage tank 162 is liquid flow connected to gas processing skid 130 and configured for pressurized storage of second processed liquid stream 62.

A blending skid 170 is liquid flow connected to first liquid storage tank 160, and liquid flow connected to a crude oil supply 34 from the tank battery 20 of an oil producing well 4, or to a secondary crude oil supply source 5 such as if remote processing system 100 is connected to a natural gas well 2 or if additional secondary crude oil supply source 5 is needed to optimize blending.

Blending skid 170 is configured for controlled blending of first processed liquid stream 60 received from first liquid storage tank 160 with crude oil 34 to form a modified crude oil product 180 having a higher API gravity and lower viscosity than the crude oil of the crude oil supply source 34 or 5.

In one embodiment, gas processing skid 130 is configured for thermal separation of compressed natural gas 42 into a first processed gas stream 50 having two carbon chain molecules or less, a first processed liquid stream 60 having five carbon chain molecules or more, and a second processed liquid stream 62 having three and four carbon chain molecules. In this embodiment, the second processed liquid stream comprises liquified petroleum gas which may be transported and sold.

Figure 5:
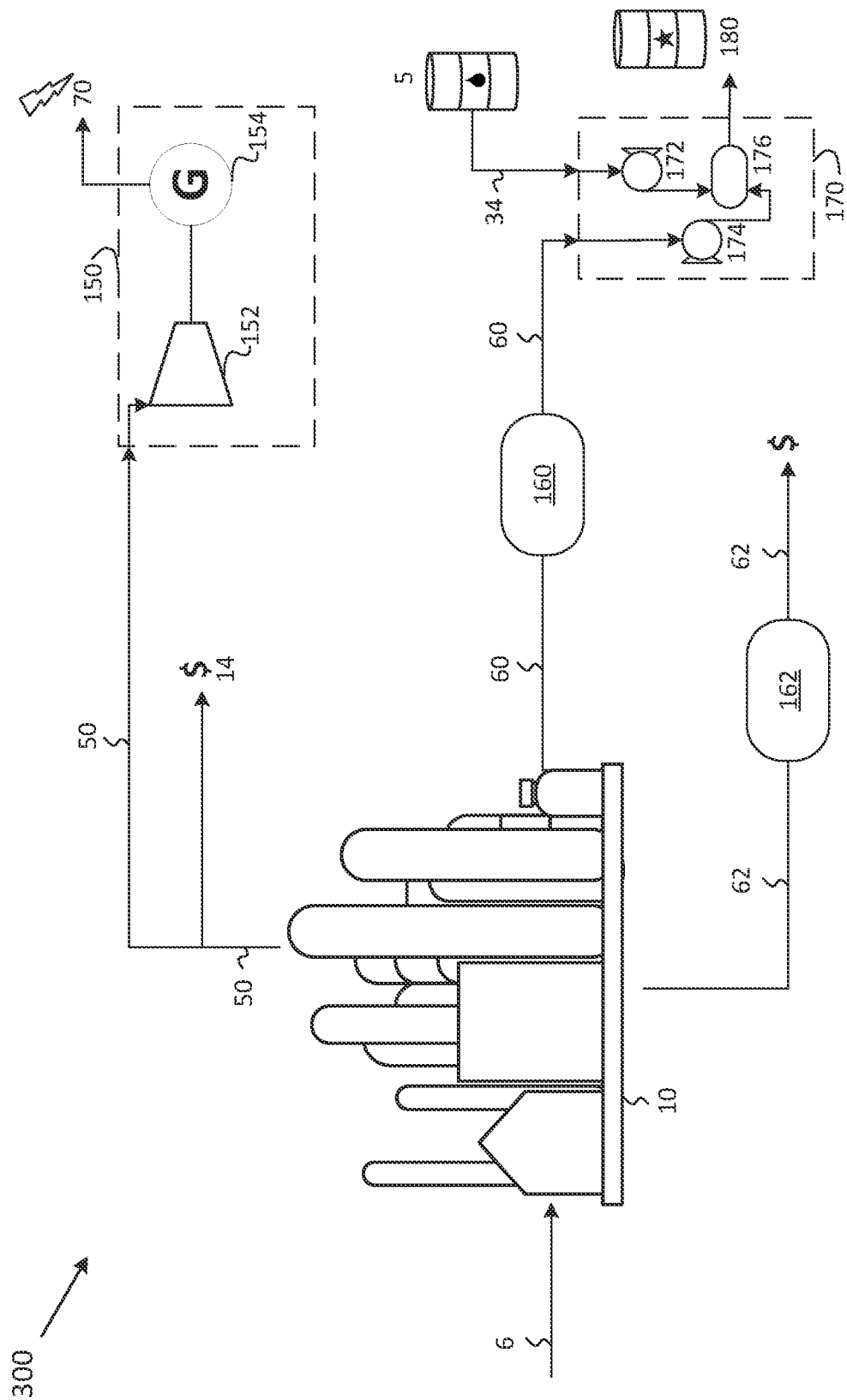
FIG. 5 is a schematic flow diagram of an embodiment of the present invention as applied for use at a central processing plant.

FIG. 5 is a schematic flow diagram of an embodiment of the present invention as applied for use at a central processing plant 10. In the embodiment illustrated in FIG. 5, a power generation skid 150 is provided for receiving a first processed gas stream 50 comprising methane and incidental ethane produced by central processing plant 10. First processed gas stream 50 is burned as fuel in a gas turbine 152 mechanically connected to a generator 154 to generate electricity. Generator 154 is connected to electrical transmission lines 70. Transmission lines 70 are connected to an electrical substation such as one located within a Competitive Renewable Energy Zones (CREZ) line zone to permit sale of the generated electricity.

A first liquid storage tank 160 may be provided to receive and store a first processed liquid stream 60 from central processing plant 10. A crude oil source 5 is provided. A blending skid 170 is provided and connected to receive crude oil 34 from crude oil source 5 and first processed liquid stream 60 from first liquid storage tank 160. Crude oil 34 and first processed liquid stream 60 are blended at blending skid 170 to form a modified crude oil product 180 having a higher API gravity and lower viscosity than crude oil 34 of crude oil source 5. Optionally, a second liquid storage tank 162 is provided for storing a second processed liquid stream 62 from central processing plant 10.

In one embodiment, first processed liquid stream 60 comprises pentane+, and second processed liquid stream 62 comprising propane & butanes. In another embodiment, first processed liquid stream 60 comprises butanes+, and second processed liquid stream 62 comprising propane. In another embodiment, a portion of first processed gas stream 50 is sold as residue gas.

Operation of the Invention

Referring to FIG. 3, a method of processing hydrocarbon products on remote wells 2 and 4 is disclosed, comprising the following steps:

Providing a gas compressor skid 110 fluid connected to the produced gas 6 of a hydrocarbon producing well 2 or 4. Providing a gas processing skid 120 fluid connected to the gas compressor skid 110. Providing a power generation skid 150 fluid connected to gas processing skid 120. Providing a liquid storage tank 160 fluid connected to gas processing skid 120. Providing a blending skid 170 fluid connected to liquid storage tank 160. Providing a crude oil 34 source, such as tank battery 20 or a secondary source 5, fluid connected to blending skid 170.

Delivering produced gas 6 from the hydrocarbon producing well 2 or 4 to gas compressor skid 110. Delivering compressed natural gas 42 from gas compressor skid 110 to gas processing skid 120. Thermally separating compressed natural gas 42 into a first processed gas stream 50 and a first processed liquid stream 60. Delivering first processed gas stream 50 to power generation skid 150. Burning first processed gas stream 50 in a turbine 152 on power generation skid 150 to drive an electrical generator 154 to generate electricity.

Delivering the first processed liquid stream 60 from gas processing skid 120 to liquid storage tank 160. Delivering first processed liquid stream 60 from liquid storage tank 160 to blending skid 170. Delivering crude oil 34 to blending skid 170. Blending first processed liquid stream 60 with the crude oil to form a modified crude oil product 180 having a higher API gravity and lower viscosity than crude oil 34.

In one embodiment, the step of thermally separating compressed natural gas 42 further comprises separating compressed natural gas 42 into a first processed gas stream 50 having four carbon chain molecules or less, and a first processed liquid stream 60 having five carbon chain molecules or more.

In one embodiment, the step of thermally separating compressed natural gas 42 further comprises separating compressed natural gas 42 into a first processed gas stream 50 having three carbon chain molecules or less, and a first processed liquid stream 60 having four carbon chain molecules or more.

A typical field operation of invention 100 in this embodiment with optimized equipment installed would include an inlet gas stream entering compressor skid 110 of 1000 MSCFD, at a pressure of 50 psig, 100° F. temperature, having a heating value of 1315 BTU/SCF, and comprising 7 gallons per MCF (GPM) of natural gas liquids (NGLs). Following gas processing, a first processed liquid stream 60 of approximately 12.7 barrels per day (BOPD) of butanes+ would be recovered at a vapor pressure of 29.7 psia and an API gravity of 92. First processed liquid stream 60 would then be blended with an approximate volume of 100 BOPD of API gravity 42 crude oil 34, resulting in a blended volume of 113.7 BOPD of API gravity 48 modified crude oil 180.

Maximum API gravity for the crude oil pipeline specification to avoid a penalty deduction of incremental evaporation and shrinkage is API gravity 50. First processed gas stream 50 would exit gas processing skid 120 following the removal of first processed liquid stream 60 (the butanes+ in this example). First processed gas stream 50 (comprising methane, ethane, and propane) would produce approximately 985 MSCFD of 1275 BTU/SCF hydrocarbon gas at 104° F. and 260 psia to be utilized as fuel in power generator skid 150. This will result in the generation of approximately 3.5 MW of electricity.

The above approximations are developed from calculations available to professionals in the oil and gas industry and can be replicated for application to all embodiments disclosed herein.

In one embodiment, the step of thermally separating compressed natural 42 gas further comprises separating compressed natural gas 42 into a first processed gas stream 50 having two carbon chain molecules or less, and a first processed liquid stream 60 having three carbon chain molecules or more.

Referring to FIG. 4, a method of processing hydrocarbon products on remote wells 2 and 4 is disclosed, comprising the following steps:

Providing a gas compressor skid 110 fluid connected to produced gas 6 of hydrocarbon producing well 2 or 4. Providing a gas processing skid 130 fluid connected to gas compressor skid 110. Providing power generation skid 150 fluid connected to gas processing skid 130. Providing first liquid storage tank 160 fluid connected to gas processing skid 130. Providing a second liquid storage tank 162 fluid connected to gas processing skid 130.

Providing a blending skid 170 fluid connected to liquid storage tank 160. Providing a crude oil 34 source, such as tank battery 20 or a secondary source 5, fluid connected to blending skid 170. Delivering produced gas from the hydrocarbon producing well 2 or 4 to gas compressor skid 110. Delivering compressed natural gas 42 from gas compressor skid 110 to gas processing skid 130. Thermally separating compressed natural gas 42 into first processed gas stream 50 and first processed liquid stream 60. Delivering first processed gas stream 50 to power generation skid 150. Burning first processed gas stream 50 in a turbine 152 on power generation skid 150 to drive an electrical generator 154 to generate electricity.

Delivering the first processed liquid stream 60 from gas processing skid 130 to first liquid storage tank 160. Delivering first processed liquid stream 60 from first liquid storage tank 160 to blending skid 170. Delivering crude oil 34 to blending skid 170. Blending first processed liquid stream 60 with the crude oil to form a modified crude oil product 180 having a higher API gravity and lower viscosity than crude oil 34. Delivering the second liquid stream 62 from gas processing skid 130 to second liquid storage tank 162.

In one embodiment, the step of thermally separating compressed natural gas 42 further comprises separating compressed natural gas 42 into a first processed gas stream 50 having two carbon chain molecules or less, a first processed liquid stream 60 having five or more carbon chain molecules, and a second processed liquid stream 62 having between three and four carbon chain molecules. In this embodiment, second processed liquid stream 62 comprises liquified petroleum gas (LPG).

In another embodiment, a method of processing hydrocarbon products on remote wells 2 and 4 is disclosed, comprising the following steps:

Providing a gas compressor skid 110 proximate to a natural gas 6 or associated natural gas 6 producing well 2 or 4. Providing a gas processing skid 130 proximate to gas compressor skid 110. Providing a power generation skid 150 proximate to gas processing skid 130. Providing a first liquid storage tank 160 proximate to gas processing skid 130.

Providing a second liquid storage tank 162 proximate to gas processing skid 130. Providing a blending skid 170 proximate to first liquid storage tank 160. Providing a crude oil 34 source proximate to blending skid 170. Delivering produced natural gas 6 from the producing well 2 or 4 to gas compressor skid 110. Delivering compressed natural gas 42 from gas compressor skid 110 to gas processing skid 130. Thermally separating compressed natural gas 42 into three hydrocarbon streams being a first processed gas stream 50, a first processed liquid stream 60, and a second processed liquid stream 62.

Delivering first processed gas stream 50 to power generation skid 150 and burning first processed gas stream 50 in a turbine 152 on power generation skid 150 to drive an electrical generator 154 to generate electricity.

Delivering first liquid stream 60 from gas processing skid 130 to first liquid storage tank 160. Delivering first processed liquid stream 60 from first liquid storage tank 160 to blending skid 170. Delivering crude oil 34 from crude oil source 20 or 5 to blending skid 170. Blending first processed liquid stream 60 with crude oil 34 to form a modified crude oil product 180 having a higher API gravity and lower viscosity than crude oil 34. Delivering second liquid stream 62 from gas processing skid 130 to second liquid storage tank 162.

In another embodiment, the step of thermally separating compressed natural gas 42 further comprises separating compressed natural gas 42 into first processed gas stream 50 having two carbon chain molecules or less, first processed liquid stream 60 having five or more carbon chain molecules, and second processed liquid stream 60 having between three and four carbon chain molecules. In another embodiment, the step of second processed liquid stream 62 comprising Liquified Petroleum Gas (LPG).

Referring to FIG. 5, a method of processing hydrocarbon products at a central processing plant 10 is disclosed, comprising the steps of:

Producing a first processed gas stream 50 comprising methane and incidental ethane. Delivering first processed gas stream 50 to an electric power generation skid 150. Burning the first processed gas stream 50 as fuel in a gas turbine 152 mechanically connected to a generator 154 to generate electricity. Delivering the generated electricity to electrical transmission lines 70 connected to a commercially available electric power grid.

Producing a first processed liquid stream 60. Providing a crude oil source 5. Delivering crude oil 34 and first processed liquid stream 60 to a blending skid 170. Blending first processed liquid stream 60 with crude oil 34 to form a modified crude oil product 180 having a higher API gravity and lower viscosity than crude oil 34 of crude oil source 5. Producing a second processed liquid stream 62 comprised of propane and butane liquids for sale as LPG.

In one embodiment, first processed liquid stream 60 comprises pentane+, and second processed liquid stream 62 comprising propane & butanes. In another embodiment, first processed liquid stream 60 comprises butanes+, and second processed liquid stream 62 comprising propane. In another embodiment, a portion of first processed gas stream 50 is sold as residue gas.

In another embodiment, a method of processing hydrocarbon products at a central processing plant 10 is disclosed, comprising the steps of:

Producing a first processed gas stream 50 comprising methane and incidental ethane. Delivering first processed gas stream 50 to an electric power generation skid 150. Burning the first processed gas stream 50 as fuel in a gas turbine 152 mechanically connected to a generator 154 to generate electricity. Delivering the generated electricity to electrical transmission lines 70 connected to a commercially available electric power grid.

Producing a first processed liquid stream 60 comprising propane+. Providing a crude oil source 5. Delivering crude oil 34 and first processed liquid stream 60 to a blending skid 170. Blending first processed liquid stream 60 with crude oil 34 to form a modified crude oil product 180 having a higher API gravity and lower viscosity than crude oil 34 of crude oil source 5.

As illustrated, the invention provides a unique solution to the engineering constraints and challenges of eliminating the flaring 38 of associated produced gas 6 in the oil and gas industry, and to provide an enhanced crude oil product 180. In particular, the invention provides a unique solution that is properly sized and configured to accommodate well 4's declining production rate while concurrently maximizing utilization of the hydrocarbon components of well 4's associated produced gas.

As used herein, the term "substantially" is intended for construction as meaning "more so than not."

Having thus described the present invention by reference to certain of its preferred embodiments, it is noted that the embodiments disclosed are illustrative rather than limiting in nature and that a wide range of variations, modifications, changes, and substitutions are contemplated in the foregoing disclosure and, in some instances, some features of the present invention may be employed without a corresponding use of the other features. Many such variations and modifications may be considered desirable by those skilled in the art based upon a review of the foregoing description of preferred embodiments. Accordingly, it is appropriate that the appended claims be construed broadly, and in a manner consistent with the scope of the invention. As used herein, crude oil and crude oil blends are always intended to be referenced as liquids. Butanes are a common industry designation for the combination of isobutane and normal butane.

The invention claimed is:

1. A method of processing hydrocarbon products at a central processing plant, comprising the steps of:
   producing a first processed gas stream comprising methane and incidental ethane;
   delivering the first processed gas stream to an electric power generation skid;
   burning the first processed gas stream as fuel in a gas turbine mechanically connected to a generator to generate electricity;
   delivering the generated electricity to electrical transmission lines connected to a commercially available electric power grid;
   producing a first processed liquid stream;
   providing a crude oil source;
   delivering crude oil and the first processed liquid stream to a blending skid;
   blending the first processed liquid stream with the crude oil to form a modified crude oil product having a higher API gravity and lower viscosity than the crude oil of the crude oil source; and,
   producing a second processed liquid stream comprised of propane and butanes liquids for sale as LPG.

2. The method of claim 1, further comprising:
   the first processed liquid stream comprising pentane+; and,
   the second processed liquid stream comprising propane & butanes.

3. The method of claim 1, further comprising:
   the first processed liquid stream comprising butanes+; and,
   the second processed liquid stream comprising propane liquid.

4. The method of claim 1, further comprising:
   a portion of the first processed gas stream being sold as residue gas.

5. A method of processing hydrocarbon products at a central processing plant, comprising the steps of:
   producing a first processed gas stream comprising methane and incidental ethane;
   delivering the first processed gas stream to an electric power generation skid;
   burning the first processed gas stream as fuel in a gas turbine mechanically connected to a generator to generate electricity;
   delivering the generated electricity to electrical transmission lines connected to a commercially available electric power grid;
   producing a first processed liquid stream comprising propane+ liquids;
   providing a crude oil source;
   delivering crude oil and the first processed liquid stream to a blending skid; and,
   blending the first processed liquid stream with the crude oil to form a modified crude oil product having a higher API gravity and lower viscosity than the crude oil of the crude oil source.

* * * * *